United States Patent
Zhou et al.

(10) Patent No.: US 11,547,296 B2
(45) Date of Patent: Jan. 10, 2023

(54) PRISM ARRAY AND APPARATUS FOR EYE-IMAGING SYSTEM

(71) Applicant: Natus Medical Incorporated, Pleasanton, CA (US)

(72) Inventors: Yan Zhou, Pleasanton, CA (US); Willem Crone, Malin, OR (US); John Allison, Pleasanton, CA (US)

(73) Assignee: Natus Medical Incorporated

( * ) Notice: Subject to any disclaimer, the term of this patent is extended or adjusted under 35 U.S.C. 154(b) by 343 days.

(21) Appl. No.: 16/947,547

(22) Filed: Aug. 6, 2020

(65) Prior Publication Data

US 2021/0106223 A1   Apr. 15, 2021

Related U.S. Application Data

(63) Continuation of application No. 15/929,777, filed on May 21, 2020, now Pat. No. 11,426,071.

(60) Provisional application No. 62/913,706, filed on Oct. 10, 2019.

(51) Int. Cl.
| | |
|---|---|
| *A61B 3/14* | (2006.01) |
| *A61B 3/12* | (2006.01) |
| *A61B 3/00* | (2006.01) |
| *A61B 3/125* | (2006.01) |
| *F21V 8/00* | (2006.01) |

(52) U.S. Cl.
CPC .............. *A61B 3/14* (2013.01); *A61B 3/0008* (2013.01); *A61B 3/125* (2013.01); *A61B 3/1208* (2013.01); *A61B 3/1241* (2013.01); *G02B 6/0008* (2013.01)

(58) Field of Classification Search
CPC ....... A61B 3/14; A61B 3/0008; A61B 3/1208; A61B 3/1241; A61B 3/125; G02B 6/0008
See application file for complete search history.

(56) References Cited

U.S. PATENT DOCUMENTS

| | | | | |
|---|---|---|---|---|
| 4,265,519 A | * | 5/1981 | Pomerantzeff | A61B 3/12 351/205 |
| 4,357,088 A | * | 11/1982 | Pomerantzeff | A61B 3/125 396/18 |
| 4,403,273 A | * | 9/1983 | Nishioka | A61B 1/00096 385/115 |
| 4,410,244 A | * | 10/1983 | Remijan | G01B 9/02 356/521 |
| 4,541,697 A | * | 9/1985 | Remijan | G01B 9/02057 351/205 |

(Continued)

OTHER PUBLICATIONS

Notice of Allowance issued in related U.S. Appl. No. 15/929,777 dated Jun. 8, 2022: 12 pages.

*Primary Examiner* — William R Alexander
*Assistant Examiner* — Sharrief I Broome
(74) *Attorney, Agent, or Firm* — Daniel C. Pierron; Widerman Malek, PL

(57) ABSTRACT

A prism array light redistribution apparatus for an eye imaging system including light transmitting fibers, light receiving fibers, and a micro prism array optically coupled to bridge the light transmitting fibers and the light receiving fibers. The array may be further configured to receive light having a bell-shaped angular distribution from the light transmitting fibers and refract the received light to enter the light receiving fibers such that a square-shaped angular distribution of light emits from a light emitting end of the light receiving fibers.

20 Claims, 9 Drawing Sheets

(56) References Cited

U.S. PATENT DOCUMENTS

| | | | | |
|---|---|---|---|---|
| 5,822,036 | A * | 10/1998 | Massie | A61B 3/125 351/219 |
| 5,852,692 | A * | 12/1998 | Nightingale | G02B 6/421 385/43 |
| 2002/0045811 | A1 * | 4/2002 | Kittrell | G02B 6/4296 606/7 |
| 2008/0015553 | A1 * | 1/2008 | Zacharias | A61F 9/008 606/4 |
| 2014/0078467 | A1 * | 3/2014 | Su | A61B 3/0008 351/207 |
| 2016/0238784 | A1 * | 8/2016 | Logunov | G02B 6/02366 |
| 2018/0372940 | A1 * | 12/2018 | Ishii | G02B 6/0031 |

* cited by examiner

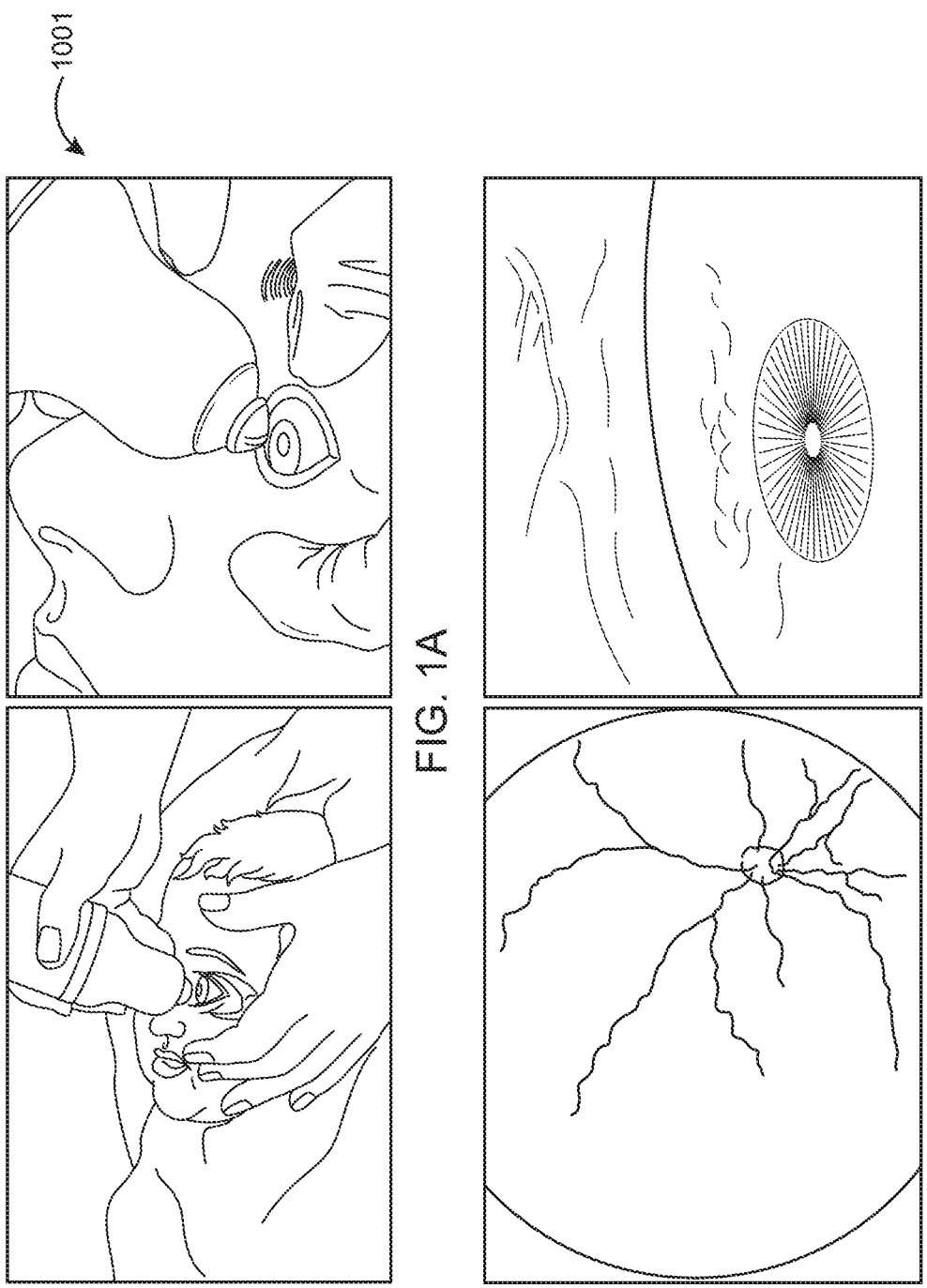

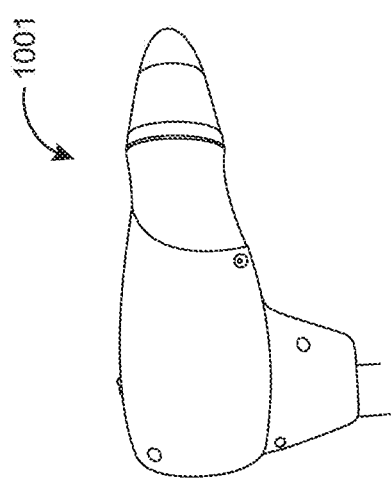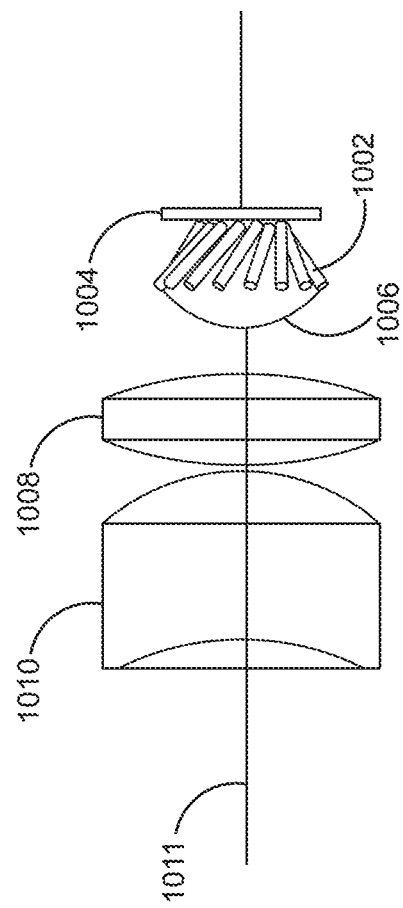

PRISM ARRAY AND APPARATUS FOR EYE-IMAGING SYSTEM

RELATED APPLICATION DATA

This application claims priority to and is a continuation of U.S. patent application Ser. No. 15/929,777 titled Eye-imaging System and Apparatus filed May 21, 2020, which in turn claims priority to U.S. Provisional Patent Application 62/913,706, filed Oct. 10, 2019, to which this application also claims priority, the details of which are incorporated herein in their entireties except to the extent disclosure therein is inconsistent with disclosure herein.

TECHNICAL FIELD OF THE INVENTION

An eye imaging system and apparatus related to uniform illumination of a patient eye. In particular, an eye imaging system and apparatus which uses a sensor for imaging and various illumination devices for lighting.

BACKGROUND

The present invention relates to ophthalmoscopes, operation microscopes and other instruments for viewing and imaging the interior of the human eye. More particularly, the invention provides an illumination apparatus and system serving to provide improved illumination over a large angular field of view for diagnostic and documentation purposes of the human eye, with the possibility of avoiding hazy or low contrast images, bright and/or dark illumination spots, and the need of large pupil dilation, therefore bypassing illumination difficulties due to, for example, a relatively small-dilated pupil.

Cameras for imaging the eye must meet several technical objectives. It is preferable, and for some clinical diagnoses required, to obtain color images of the eye. Also, in some instances such as fluorescence angiography, blue excitation induced fluorescence images are required. For some applications, an eye imaging camera should offer the option of providing very high spatial resolution for diagnosis of certain ocular diseases. For example, when examining the neural fiber layer, high resolution is required.

Moreover, wide field-of-view (FOV) images of the eye are necessary for evaluating some pathologies of the eye. Exemplar pathologies include, but are not limited to, retinopathy of prematurity (ROP) where the demarcation line between avascular retina and vascularized retina occurs often on the peripheral region of the retina, and ocular tumors which, in many cases, lie on or spread to the periphery of the retina. When examining only the optical disk, a 30 degree wide FOV is sufficient. For studies of ROP and tumors located on the periphery of the retina and other optical disorders, a FOV of 120 degrees and even larger is preferred. The intensity of light required for imaging is also a consideration as light safety requirements need to be met. Scattering and reflection of the illumination light from ocular structures other than the retina can also substantially reduce the contrast of the image. Imaging using electronic array sensors such as Complementary Metal Oxide Semiconductor (CMOS) and charged coupled devices (CCD) instead of film is highly desired as well. Electronic sensor array-based cameras tend to be more sensitive than film, reducing the amount of illumination light required. Electronic sensors and displays also allow instant and live review of the image, in addition to possibly providing various image processing operations without a noticeable time delay.

As described in the art, in order to image the eye a system must optically relay the spherical concave retina onto a flat image sensor (2D) plane. Further to the above, in conventional systems background haze is created when the light used to illuminate the retina is reflected and/or scattered by the cornea and ocular lens such that they are channeled to the image sensor. These reflections are also known as Purkinje images. A "first Purkinje image" is the reflection from the outer surface of the cornea, the second is the reflection from the inner surface of the cornea, the third is the reflection from the outer surface of the ocular lens, and the fourth emanates from the inner surface of the ocular lens. As described in the art, the first Purkinje image may be mostly avoided with careful control of positioning of an imaging device near the patient's eye and with the use of optical coupling gel between the device and the cornea. Further, subsequent Purkinje images need to be removed in the post process phase and/or minimized from appearing on the image in the first place.

Systems have been developed to minimize the effect of Purkinje images during ophthalmic visualization. In one such system, the light emitted from the lenspiece of an ophthalmoscope is conditioned by a relatively large inner diameter optical fiber annular array ends through a micro-structured light guide or diffuser. However, this creates a side effect of reducing the amount of light transmitted and creating scattered light, which can negatively impact certain eye examinations, such as those for retinopathy of prematurity (ROP) in premature infants, which require a wide field of view. In addition, the larger diameter of the optical fiber array and the corresponding micro-structured light guide or diffuser imposes the need for a larger pupil size.

In addition, prior art related to illuminating a large angular field of view for uniform illuminator imaging includes the use of various micro-structured light conditioning optical elements arranged in between the front most optical element (the contact lens) of the imaging device and a circular array of optical fibers or free space optical designs to redistribute the illumination light before light enters an eye. Currently, most of the uniform illuminator viewing and imaging systems illuminate the interior of the eye through the pupil of the eye by a light source that is channeled to land as a ring around the imaging path near the cornea and is directed into the posterior segment of the eye.

Moreover, when used to obtain color images of the retina, these systems apply light sources that produce light containing blue (B), green (G), and red (R) wavelengths. Because the retina is illuminated through the pupil of the eye, these systems can suffer from light illumination reflections off the cornea, ocular lens, and its interface with the vitreous cavity. They need typically more than half of the pupil area for illumination, and when attempting to view portions of the interior of the eye more peripheral than the macula, the effective pupil size that is available becomes smaller and light is not transmitted through. As a result, standard uniform illuminator viewing and imaging systems depend strongly on clear ocular media and on wide pupil dilation and they are limited to a maximum of 60° field of view and cannot observe the periphery much beyond the posterior pole.

To avoid the unwanted illumination light reflections from landing on the image sensor, the illumination ring at the cornea and ocular lens region is generally arranged to land outside the imaging path. Polarization means has also been used to reduce these light illumination reflections. Examples of such systems include U.S. Pat. Nos. 5,822,036, 8,836, 778, 9,351,639, 9,872,618 and 10,258,232. A common issue associated with these designs is that the illumination on the retina has limited uniformity or limited field of view. In general, on the image sensor plane, a donut shaped illumination distribution is detected, leading to darker illumination at the peripheral and central regions than at mid field of view regions.

The problems associated with illuminating the interior of the eye through the pupil can be avoided when the interior of the eye is illuminated through the sclera (synchronized sequential color illumination), as first proposed by Pomerantzeff in U.S. Pat. No. 3,954,329. This system supports the use of a low cost monochrome image sensor and wide angle uniform illuminator imaging without demanding pupil dilation and while bypassing illumination difficulties that may rise due to obstruction and scattering from opacities in the anterior eye chamber and any other intervening ocular structures. Relatedly a system (Panoret-1000™ of Medibell Medical Vision Technologies, Ltd.) that is based on U.S. Pat. No. 5,966,196 (Svetliza, et al.) and U.S. Pat. No. 6,309,070 (Svetliza, et al.) has applied synchronized sequential color illumination according to the method disclosed in the '329 patent referenced above.

However, illuminating through the sclera requires much higher optical power or energy than illuminating through the pupil and there exists a possibility that the unsafe strong illumination light is transmitted through the pupil. This can happen when live imaging is ongoing while a handheld image capture unit is moved around relative to a patient eye while a live video display of the retina image is being monitored. In addition, blue light, which is much more hazardous to a patient eye, can be substantially more absorbed than red and green light by the sclera. As a result, more blue illumination light is needed, which is an even less safe circumstance for the patient.

Given the above-mentioned limitations and/or issues, there exists a need for improvement in illumination uniformity for wide angular field of view optical imaging systems. Accordingly, it is a first object of this invention to provide an eye-imaging apparatus and a system for obtaining images of the interior of the eye with improved illumination uniformity and substantially reduced background light noise. The uniformly illuminating eye-imaging apparatus and system described herein includes various light distribution conditioning means in addition to unique spectral illumination filters. In use, light is disposed along an illumination light path, ultimately forming uniformly illuminated images of a given eye locus on an image sensor plane. The uniformly illuminating eye-imaging apparatus and system employ either continuous or synchronized sequential color illumination in addition to other features resulting in redistribution of light.

It is another objective of the invention to employ a large numerical aperture (NA) optical fiber to output light with a large illuminating cone angle. Yet another embodiment employs a light re-distribution element at one or more locations along the illumination optical fiber such that the light output from the fiber end is converted from having a bell-shape intensity distribution to one having a hat-top intensity distribution. Still another approach directs the illumination light from each coordinated illuminator fiber end (i.e., an illumination optical fiber end) at a skewed angle to enter the eye such that illumination light reflections from the cornea and ocular lens optical interfaces are mostly directly away from the imaging path. As a result, the inner diameter of the annular fiber array can be smaller than that of the prior art, thus reducing the need for a relatively large pupil size. Each of the embodiments can be implemented independently or combined with other approach(es) known in the art. Further to the above, the present invention relies on various light distribution elements and uniquely-arranged aperture fibers.

The illuminator fibers may include a high numerical aperture and further include circular fiber array ends arranged at a skewed angle relative to the optical axis of the imaging path. Said skewed angle relative to the optical axis of the imaging path may be at least 30 degrees, 35 degrees, 40 degrees, or the like. Said light redistribution element may be a micro-prism array disposed along the optical fiber illumination light path. Said illuminator fibers (also referred to herein as "fibers" or "plastic fibers") are of at least 0.60 NA and include an illumination variation of less than or equal to at least twenty five percent variation in the preferred embodiment. Further, the invention may comprise an imaging device comprising one or more lenspiece(s) that can be mechanically connected to a common handpiece, and the handpiece may include a visual wavelength image sensor, an optical path length compensation window, a deep red and/or near infrared cut filter, and an axially movable lens combination for focusing and relaying a real image. Finally, the illuminator fibers may be shielded by a light blocking tube on the outside of the cladding or coated in black paint on the outside of the cladding and may be perpendicularly cut off at the illuminator fiber tips in some embodiments.

BRIEF DESCRIPTION OF THE DRAWINGS

In order to enhance and improve understanding of the various elements and embodiments of the invention, elements in the figures have not necessarily been drawn to scale. Furthermore, elements that are known to be common and well-understood to those in the industry are not depicted in order to provide a clear view of the various embodiments of the invention. Thus, the drawings are generalized in form in the interest of clarity and conciseness.

FIG. 1A depicts an imaging head of a handheld uniform illumination eye imaging device being positioned close to the eye of a patient with the light coupling medium adherent to the imaging lenspiece for imaging respectively the retina and the anterior chamber of the eye according to one embodiment of the present invention.

FIG. 1B depicts respectively a retina image and an anterior chamber angle image of a patient eye according to one embodiment of the present invention.

FIG. 2A depicts a wide angular field of view uniform illumination lenspiece attached to a handpiece according to one embodiment of the present invention.

FIG. 2B depicts illumination path and imaging path optical elements of a lenspiece according to one embodiment of the present invention.

DETAILED DESCRIPTION

Figure 2C:
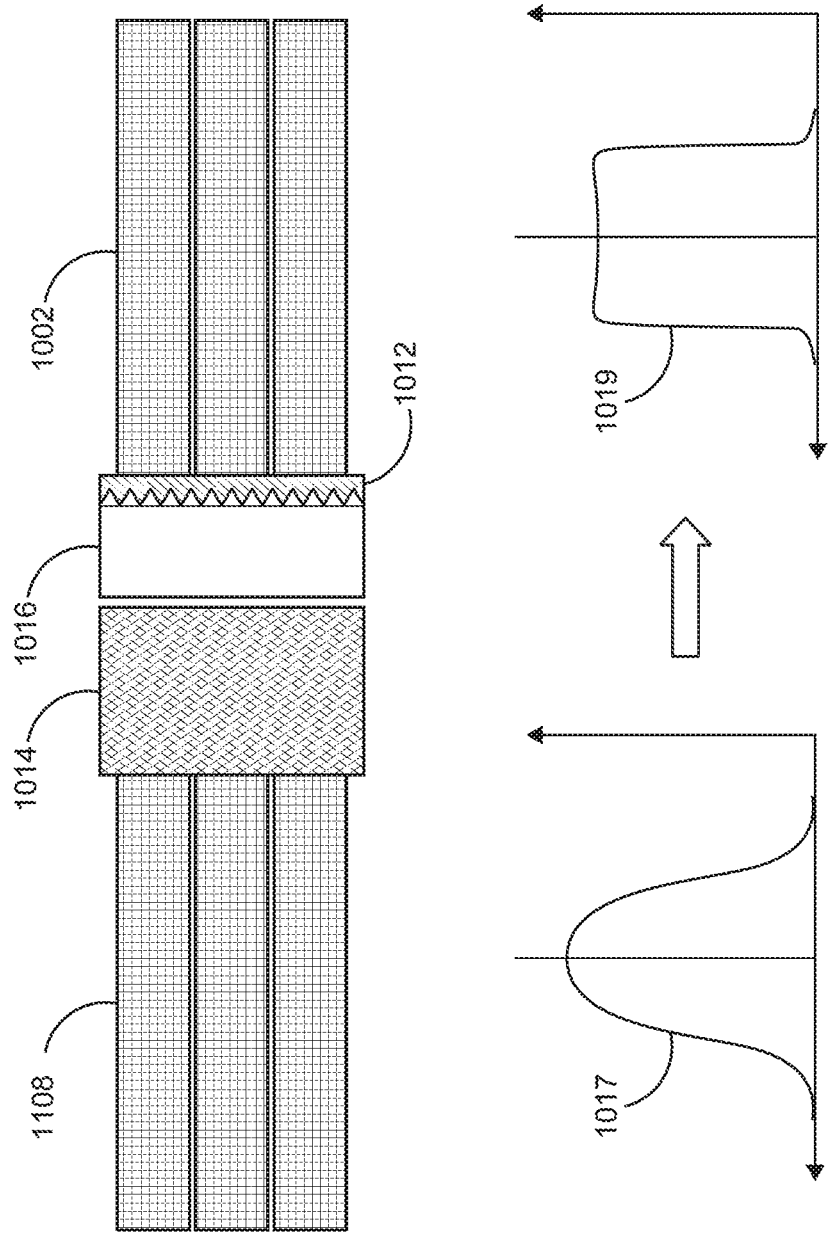
FIG. 2C shows some of the illumination path optical elements from the handpiece side to the lenspiece side, in addition to the illumination light intensity distribution change from the handpiece side to the lenspiece side according to one embodiment of the present invention.

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized, and changes may be made without departing from the scope of the present invention.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term "about" means +/−5% of the recited parameter. All embodiments of any aspect of the invention can be used in combination, unless the context clearly dictates otherwise.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". Words using the singular or plural number also include the plural and singular number, respectively. Additionally, the words "herein", "wherein", "whereas", "above", and "below" and the like shall refer to this application as a whole and not to any particular parts of the application. Notably "light" is variously referred to herein as "illumination", "illumination beam", "visual wavelength", "color", and the like.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

FIG. 1A illustrates the case when an imaging head of a conventional contact type eye imaging device is being positioned close to the eye of a patient. A light coupling medium may be used to bridge the gap between the end of the imaging lenspiece and the cornea of the patient eye. The left diagram shows how the lenspiece is held for imaging the retina and the right diagram shows how the lenspiece is held for imaging the anterior chamber. Relatedly, FIG. 1B depicts respectively the sketch of a wide-angle retina image (left) and the sketch of an anterior chamber image (right). The present invention is an improvement in that it can enable the capture of a retinal image with a wide angular field of view (up to 130 degrees in some embodiments) with substantially improved illumination uniformity. To achieve this, as one of the requirements, there is a need for an optical coupling medium to bridge the gap between the front most optical element and the cornea of a patient eye. When the light coupling medium makes contact with the cornea of the patient eye and the volume of the light coupling medium fills the space between the device and the eye, the light coupling medium will bridge the gap and optically enhance light transmission. This also helps to eliminate a significant amount of optical aberrations originating from the cornea of the eye. FIG. 1A further shows that light coupling medium permits imaging light to easily transmit through the gap, thereby facilitating ophthalmological examination.

FIG. 2A shows an embodiment of the presently invented eye-imaging apparatus 1001 including a handpiece and a lenspiece connected to each other. FIG. 2B shows the imaging path optical elements (1004, 1006, 1008 and 1010) of a lenspiece and a front part of the illumination path optical elements (an array of optical fibers 1002 positioned next to a contact lens 1004 with the fibers skewed at an angle relative to the image path optical axis 1011) of the lenspiece. Illuminator fibers 1002 generally comprise light-transmitting fibers. In some embodiments, plastic multimode optical fibers like the Toray RAYTELA Polymer Optical Fiber PQE-FB 750 are used that have a diameter of 0.75 mm and an NA (numerical aperture) of 0.64. While plastic fibers are mentioned, optic fibers of any type are contemplated and included within the scope of the invention, including glass fibers. The skewed circularly arrayed fibers 1002 are arranged next to each other at the front of the conic lens 1006. The maximum number of fibers of the array 1002 that can be arranged next to each other at the front of the conic lens 1006 is dependent on the fiber diameter, the half cone angle and the front diameter of the conic lens 1006, and the skew angle of the fibers relative to the optical axis 1011. In one embodiment, the front diameter of the conic lens 1106 is about 3.5 mm, the half cone angle of the conic lens 1006 is about 30 degrees, the skew angle of the fibers 1002 relative to the optical axis 1011 is about 40 degrees, and 16 fibers are arranged at the front of the conic lens 1006 next to the contact lens 1004. Such a design will ensure that Purkinje reflections of the illumination light are substantially directed away from entering the imaging path. At the same time, the illumination ring at the iris plane can be relatively small (less than 4.5 mm in the outer diameter of the annular illumination ring there) so the required minimum pupil dilation size for good illumination is about 4.5 mm only.

FIG. 2C shows a micro prism array film based light intensity profile redistribution element (referred to hereafter as, "MPAR") 1012 that is disposed between the light-transmitting fibers 1108 and light-receiving fibers 1002 at the intersection of the handpiece and the lenspiece. In one embodiment, MPAR 1012 is arranged on the lenspiece side (the right side), optically in connection with the transmitting fibers 1108 on the handpiece side. The arrangement enables illumination light to be initially guided through the transmitting fibers 1108, angularly redistributed as light passes through the MPAR 1012, and then received at a receiving end by the receiving fibers 1002. As a result, when light emits from an emitting end at the other side of the receiving fibers 1002, the light intensity angular distribution is changed relative to that from the transmitting fibers 1108.

In some embodiments, the present invention contemplates optic fiber with a large Numerical Aperture (NA), numerical aperture being the characterization of the range of angles over which the optic fiber receives and emits light. For example, receiving fibers 1002 and transmitting fibers 1108 may be fibers with numerical aperture of at least 0.60 NA. In some embodiments, the receiving and transmitting fibers 1002, 1108 may have numerical apertures of 0.64 NA. In one embodiment, the illumination light path initially has a total of 30 plastic fibers that receive light from a light source like an LED light box. These fibers can be in the form of a light guide cable to transmit light to the handpiece, and inside the handpiece it is then split into two sub-cables, each with 15 fibers. At the optical interconnect from the handpiece to the lenspiece, each 15-fiber-port from the handpiece is connected to an 8-fiber-port in the lenspiece and as a result, mechanical connection tolerance is built into the design to ensure relatively consistent light transmission and/or coupling efficiency from the handpiece to the lenspiece.

Further to the above, in one embodiment, the fibers in the lenspiece, especially the portion near the tip of the lenspiece, may have absorptive material positioned on the sides thereof, with the fiber ends being free of absorptive material by perpendicularly cutting or cleaving or lapping/polishing the fiber ends. This ensures that no light escapes from the sides of the fibers to create background optical noise in the captured image. In some embodiments, a black paint may be applied to the sides of the end of the fibers. Alternatively, the use of black or light absorbing tubing to encompass the front section of the lenspiece optical fibers can provide the same function as the black paint coating. Doing so will substantially suppress scattered illumination light at the fiber end sections from being channeled to the imaging path, therefore preventing haze or glow at the periphery in the final fundus or retina image. This approach also improves the manufacturability of the lenspiece.

In some embodiments a portrait lenspiece is provided (i.e., a separable lenspiece) for taking an external image of the patient's eye or face. When taking a picture of the patient's face there is no need for the spherical field curvature corrections as in the case of optically relaying a concave spherical retina to a flat image sensor. In such a case, the MPAR may or may not be needed on the portrait lenspiece side as illumination uniformity requirement for external patient eye or face imaging is not as critical as in the case of retina or fundus imaging.

In general, light coupled into a multimode optical fiber and then emitted from the fiber will have a bell-shaped angular optical power or intensity distribution 1017, with more power or intensity distributed around the central angular range of the light emitting cone (i.e. contained among the lower order modes). To convert a bell-shaped angular distribution to a more hat-top or square shaped angular distribution 1019, the thin prism array film (MPAR) 1012 in between the illumination light path of the handpiece and the lenspiece serve the transfer function. As shown in FIG. 2C, the angular light distribution shape changes from that of a bell shape 1017 when light emits from the handpiece fibers to that of a hat-top shape 1019 when light emits from the lenspiece fibers. As a result, the illumination light from a skewed circular array of fibers when landing on the retina can span a wide enough range with substantially improved illumination uniformity. When compared to the prior art, the optical energy will spread more to the peripheral and the center of the retina while also more uniformly covering the desired angular field of view.

Figure 6:
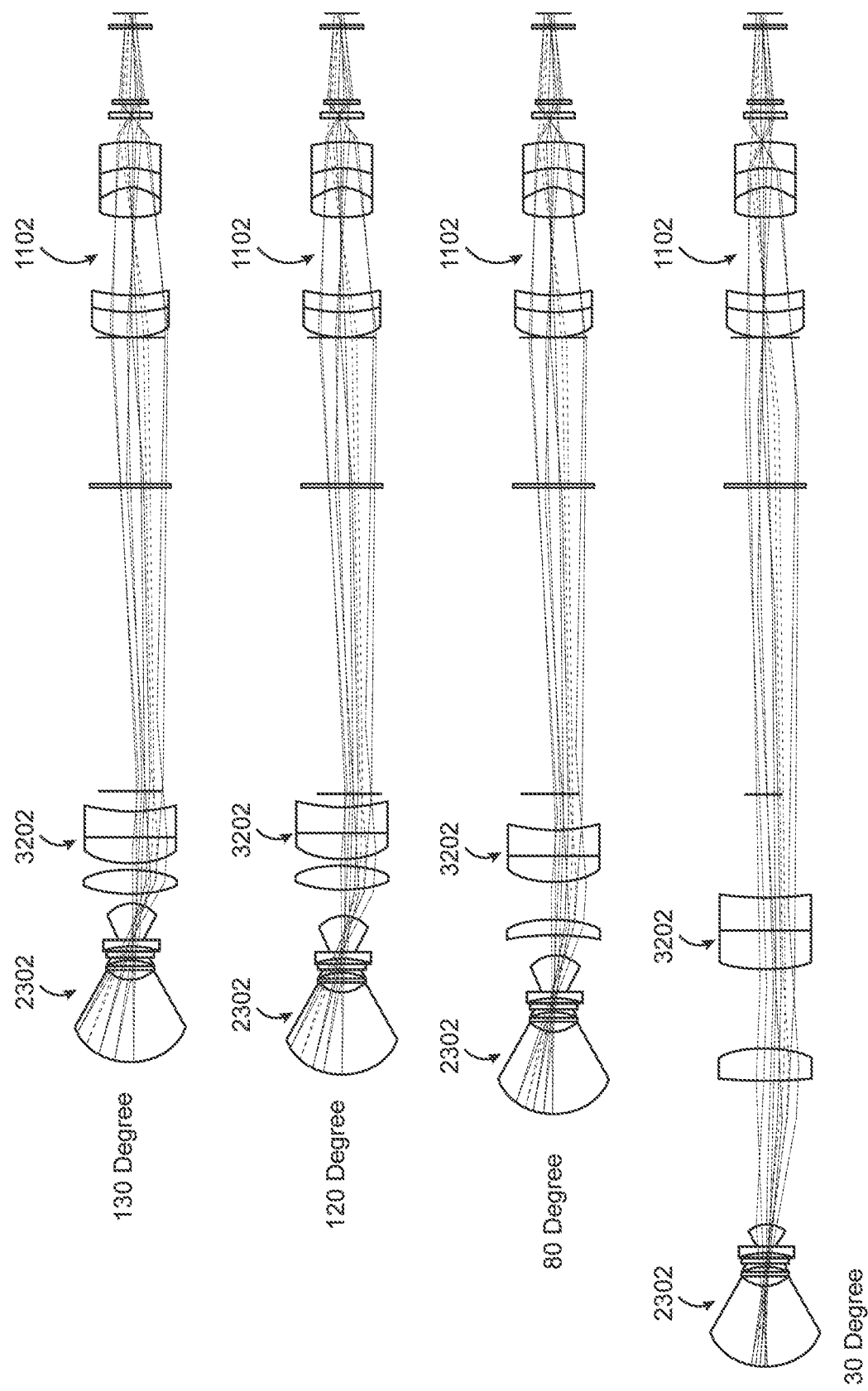
FIG. 6 depicts an imaging path optical design of an eye model with imaging optical elements inside both the handpiece and various lenspieces.

Returning to FIG. 2A, a wide angular field of view retina or fundus imaging lenspiece is shown attached to a handpiece according to one embodiment of the present invention. Notably, the device can be held next to the cornea of a patient eye and with light coupling gel, a wide angular field of view fundus image may be captured. In some embodiments, different lenspieces that are designed to image eye structures such as the retina or fundus with different angular field of views (when each of them is attached to the handpiece) may be used. FIG. 6 shows the optical designs of different lenspieces with different angular field of views being connected to the same handpiece to form different angular field of view retina or fundus images of the same infant eye.

FIG. 2B shows the optical elements at the front portion of a wide angular field of view lenspiece. Some embodiments of the present invention are such that the angle at which the light emanates from the tip of any given fiber along a light output pointing line of the fiber (being a central line of the light-emitting cone of the fiber) functions to minimize Purkinje reflections being channeled back to the imaging path. As an embodiment of the present invention, the array of illuminator fibers 1002 that terminate next to the front optical element (the contact lens) 1004 are arranged in a skewed manner. In other words, the circular fiber array ends at a skew angle relative to the lenspiece imaging path optical axis 1011 so the fibers are not on a meridional plane of the optical axis 1011 of the imaging path optical lenses, i.e. at a skewed angle relative to the optical axis 1011. Concordantly, the illuminator fibers 1002 may also be arranged such that the light output pointing lines thereof are at a skewed angle relative to each other. The imaging path optical lenses may comprise a contact lens 1004, a conic lens 1006, a mid-position singlet 1008, and a back-position doublet 1010. The contact lens 1004 may be positioned optically proximal of and in contact with the conic lens 1006, the conic lens 1006 is positioned optically proximal of the singlet 1008, and the singlet 1008 is positioned optically proximal of the doublet 1010. In some embodiments, the skew angle relative to the optical axis 1011 may be at least 30 degrees, at least 35 degrees, or at least 40 degrees. Importantly, none are on or across the meridional plane of the optical axis 1011 in said embodiments. Notably, the gap between the contact lens 1004 and the nosepiece (the front endcap housing, not known in the Figure) of the lenspiece may be sealed in the preferred embodiment, preventing liquid ingress to the lenspiece from its front end. With this skewed fiber angle arrangement, when the illumination light rays hit the front and back surfaces of the cornea and the ocular lens, most of the illumination light rays will be specularly reflected by these surfaces to not enter the imaging path and as a result will not land on the image sensor to produce background optical noise. In other words, when the illumination light beams hit the four Purkinje surfaces, the specularly reflected light rays are mostly directed away from the imaging path. As such, Purkinje images are mostly directed away and minimally captured by the image sensor.

FIG. 2C shows the illumination path optical elements at the interconnect portion between the lenspiece and the handpiece. As an embodiment of the present invention, along the illumination path at the intersection, a micro prism array film based light intensity profile redistribution element 1012 in the form of a micro-prism array film (MPAR) is disposed between the illumination light receiving fibers 1002 on the lenspiece side and the transmitting fibers 1108 on the handpiece side, optically coupling the fibers to bridge them together. In some embodiments, plastic optical fibers with high numerical apertures (for example, NA=0.64) are used. An optical window 1016 is provided on the lenspiece side to protect the MPAR 1012 and the fibers 1002. In some embodiments, a glass rod based optical homogenizer 1014 is used on the handpiece side to both homogenize the illumination light and to protect the illumination optical fibers 1108 in the handpiece. Because there are multiple optic fibers in each fiber cable or sub-cable that can cause light intensity hot spots, by sending all the illumination light through a specialized glass rod homogenizer, said light can thus achieve enhanced uniformity in spatial light intensity distribution. For example, a rod may be within a range of 3-4 mm wide or in diameter and 10 mm long. An optical window 1016 is positioned between the MPAR 1012 and the optical fibers 1002 to protect the MPAR 1012 and the optical fibers 1002 in the lenspiece. In general, light coupled into a multimode optical fiber and then emitted from the fiber will have a bell-shaped angular optical power distribution, with more power distributed around the central angular region of the light emitting cone (i.e. contained among the lower order modes). To convert a bell-shaped distribution 1017 to a more hat-top or square-shaped distribution 1019, the MPAR 1012 is used in between the handpiece and the lenspiece. The angular light distribution shape changes from that of a bell shape 1017 when light emits from the handpiece fibers 1108 to that of a hat-top shape 1019 when light emits from the lenspiece fibers 1002 after the transmission of the illumination light from the handpiece side to the lenspiece side. As a result, the illumination light from the skewed circular array of fibers 1002 (as shown in FIG. 2B) when landing on the retina can span a wide enough range with optical energy spreading more to the peripheral and the center of the retina than the bell shape distribution to more uniformly cover the desired angular field of view.

In some embodiments, in order to spread the light more evenly across the retina, a film is used containing a prism material. The film is adhered with glue or the like on either the optical window 1016 side or the optical fiber side or on both sides, and the glue has an index of refraction of the right choice that further helps to spread the light with the desired angular spreading range. The MPAR 1012 may be the 3 M™ BRIGHTNESS ENHANCEMENT FILM BEF4 GT 90/24 with a refractive index of 1.66, and the glue on the prism side may be transparent with a refractive index of 1.348. As a result, when an illumination light ray hits the glue from the prism array side, it is guided sideways, spreading out with an additional deflection angle. In some embodiments, as shown in FIG. 2C, the prism array 1012 induces the distribution of light to transform from a bell curve to more square-like curve.

Figure 3:
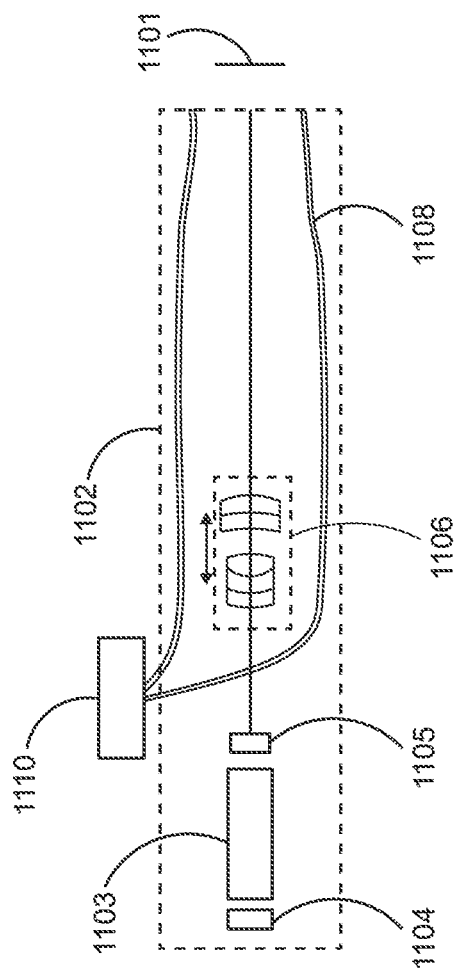
FIG. 3 illustrates a handpiece with both illumination and imaging optical elements inside the handpiece according to one embodiment of the present invention.
Figure 4:
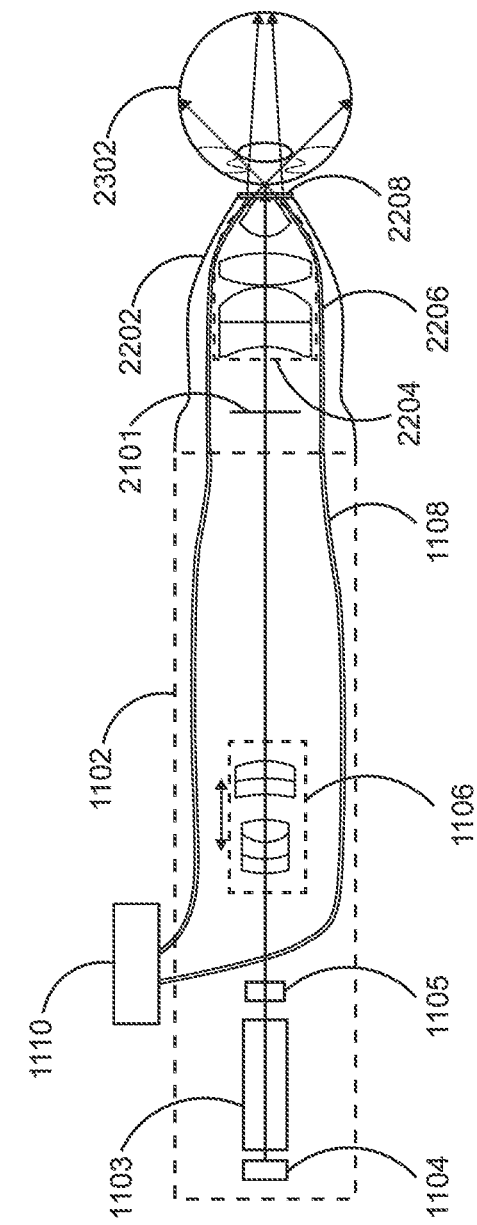
FIG. 4 depicts a patient eye positioned next to a lenspiece that is in mechanical connection with a handpiece, with the imaging optical elements and the illumination path inside both the handpiece and the lenspiece according to one embodiment of the present invention.

Referring to FIG. 3, the dashed rectangular box represents a handpiece 1102. Inside the handpiece 1102 is a visible wavelength image sensor 1104 which can be connected to a live video display (not shown), a color splitting prism block or an optical path length compensation block 1103, a deep red and/or near infrared cut filter 1105, and an axially movable lens combination 1106. The lens combination 1106 focuses and relays a real image from somewhere at or near the intermediate image plane 1101 to the image sensor 1104. The lens combination 1106 may comprise a front-position doublet and a rear-position triplet. Inside the handpiece, there is also an illumination light path comprising a number of fibers 1108 (which can be the same fiber as the fiber 1002 in the lenspiece), that can be bundled to one or more light emitting ports and terminate at the front end of the handpiece. Notably as shown in FIG. 4, in some embodiments, the imaging relay from the retina of a patient eye 2302 to the intermediate image plane 2101 is accomplished by the lenspiece, and from there the image is relayed and focused to the image sensor 1104. As discussed, fibers 1002 or 1108 may include the use of plastic fibers with high numerical aperture (NA). In some embodiments, the other ends of the fibers 1108 (also referred to herein as "illuminator fibers") can be bundled together and optically connected to a white or broadband wavelength light source, or a single-color wavelength light source. The fibers 1108 are configured to collect and couple the illumination light from the light source(s) and transmit the illumination light along the illumination path in the handpiece. The light source 1110 may be located outside or inside the handpiece.

In another embodiment, the use of fibers with high numerical aperture (NA) are contemplated. An example is the TORAY RAYTELA PQE series plastic fibers that have a numerical aperture of 0.64. Said fibers ultimately provide illumination light to the lenspiece and then from a skewed circular array of fibers at the end of the lenspiece to span a wide enough range to cover the desired angular field of view on the retina of a patient eye.

Referring to FIG. 4, the handpiece can be combined with any lenspiece of a certain angular field of view coverage designed to be used with the presently disclosed system as long as the lenspiece can form a real intermediate image at or near the intermediate image plane in front of the handpiece. In addition, in the preferred embodiment the lenspiece and handpiece achieve a wide angular field of view ("FOV") of up to 130 degrees relative to the center of the eye globe. As illustrated in FIG. 4, a 130-degree FOV lenspiece is shown attached to the handpiece as an example. On the right side of the handpiece, a cone-shaped housing 2202 represents the body of a 130-degree FOV lenspiece. Inside the lenspiece, there is a lens combination element 2204 and an illumination light path 2206 comprising a number of fibers optically coupled with those fibers in the handpiece. The front optical element 2208 can function both as a front contact lens of the lens combination 2204 for forming an intermediate image of an object at or near the intermediate image plane 2101 and as a transmission window for the illumination light as well as an optical sealing window. In some embodiments, the handpiece and lenspiece comprise an angular FOV of at least 110 degrees relative to the center of the eye globe. In other embodiments, the handpiece and lenspiece comprise an angular FOV of at least 120 degrees relative to the center of the eye globe.

Continuing with FIG. 4, a human eye 2302 is shown at the far right, with the lenspiece positioned next to the cornea and a light coupling medium (gel) filling the gap between the front contact lens 2208 and the human eye 2302. At this position, the illumination light beams coming from the ends of the optical illuminator fibers 2206 enter the eye with a skewed beam direction or angle and a flattened angular light intensity distribution, as well as a cone angle (or numerical aperture) large enough to illuminate the desired area on the retina of the eye 2302. In some embodiments, variation in angle of the lenspiece relative to the eye allows various views for optical examination. Notably, with a certain coupling gel gap distance the light rays will pass through the cornea outside the imaging path but can still enter the eye without being blocked by the iris of the human eye 2302. Standard gel gap tolerance ranges apply with respect to the cornea and the front contact lens 2208. For example, the gel gap distance can be from 0.5 mm to 1.0 mm. In some embodiments, the illumination uniformity variation as detected on the image sensor is less than or equal to twenty five percent or even less than 10%. This illumination variation is greatly reduced relative to conventional systems, which typically result in at least fifty percent variation resulting from generally a donut shaped illumination annular ring.

Figure 5:
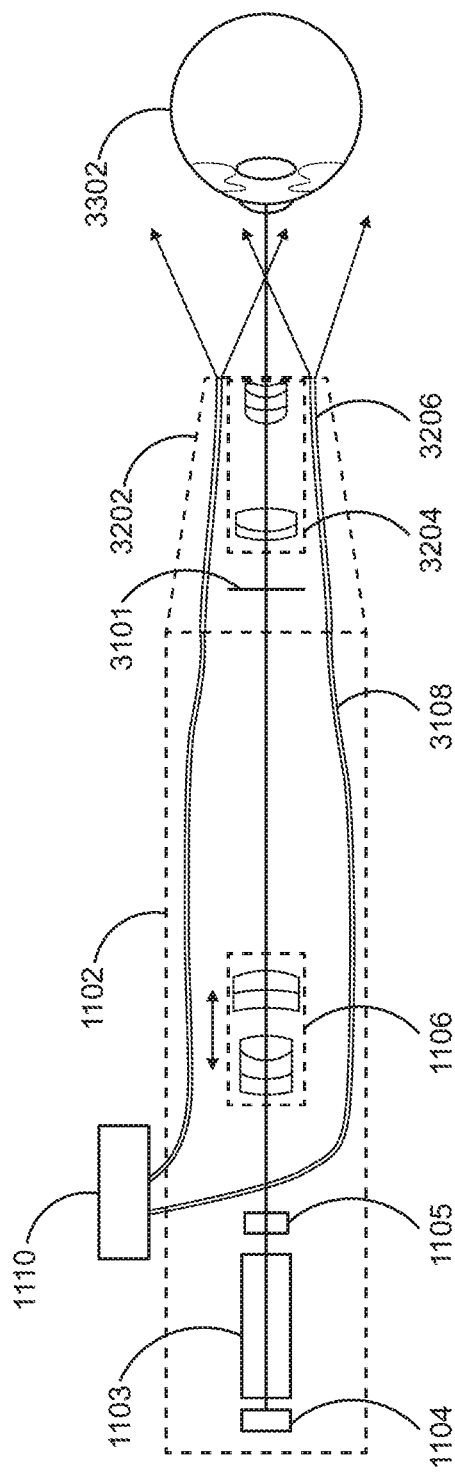
FIG. 5 depicts a patient eye positioned at a distance from a portrait lenspiece that is in mechanical connection with a handpiece, with the imaging optical elements and the illumination path inside both the handpiece and the portrait lenspiece according to one embodiment of the present invention.

Referring now to FIG. 5, there is shown the case of a portrait lenspiece 3202 attached to the handpiece 1102. Inside the portrait lenspiece is a lens combination 3204 that can form an intermediate real image of the object (an external image of a patient eye as shown in FIG. 5) at or near the intermediate image plane 3101. There is also an illumination light path 3206 comprising a number of fibers or fiber bundles that relay the illumination light from the handpiece to the portrait lenspiece and exit the portrait lenspiece to flood illuminate an object. In this case, there is a relatively large air gap between the portrait lenspiece 3202 and the patient eye 3302, and no coupling gel is used. The illumination light from the optical illuminator fibers 3206 can be bundled into four light emitting ports and spread to illuminate the external of the patient eye 3302. Depending on the air gap distance, a larger or smaller external feature of the patient eye or the patient face may be illuminated and digitally imaged.

Figure 7A:
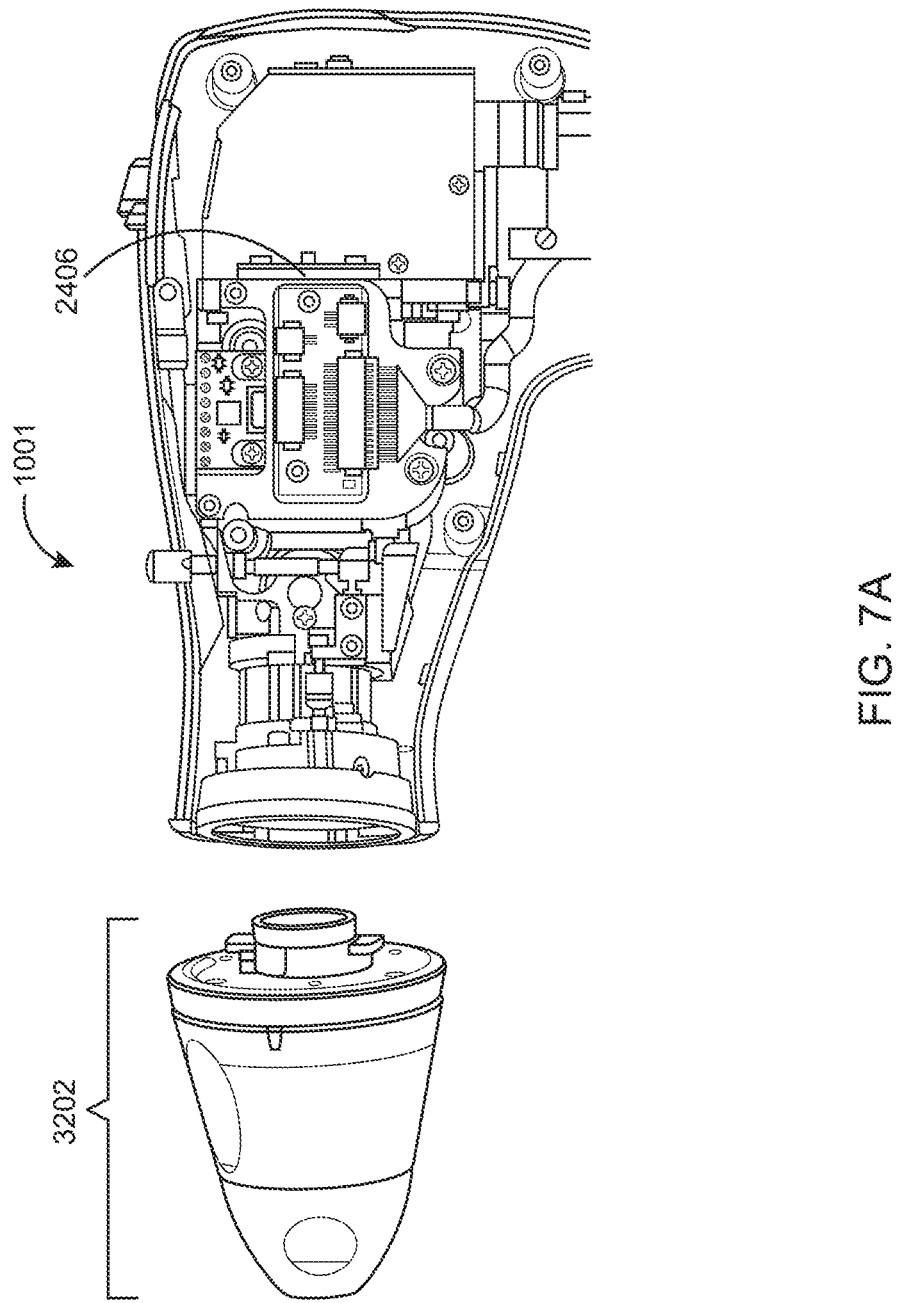
FIG. 7A depicts a lenspiece just separated from a handpiece, including a detailed exterior view of the lenspiece in addition to a detailed view of the handpiece core.
Figure 7B:
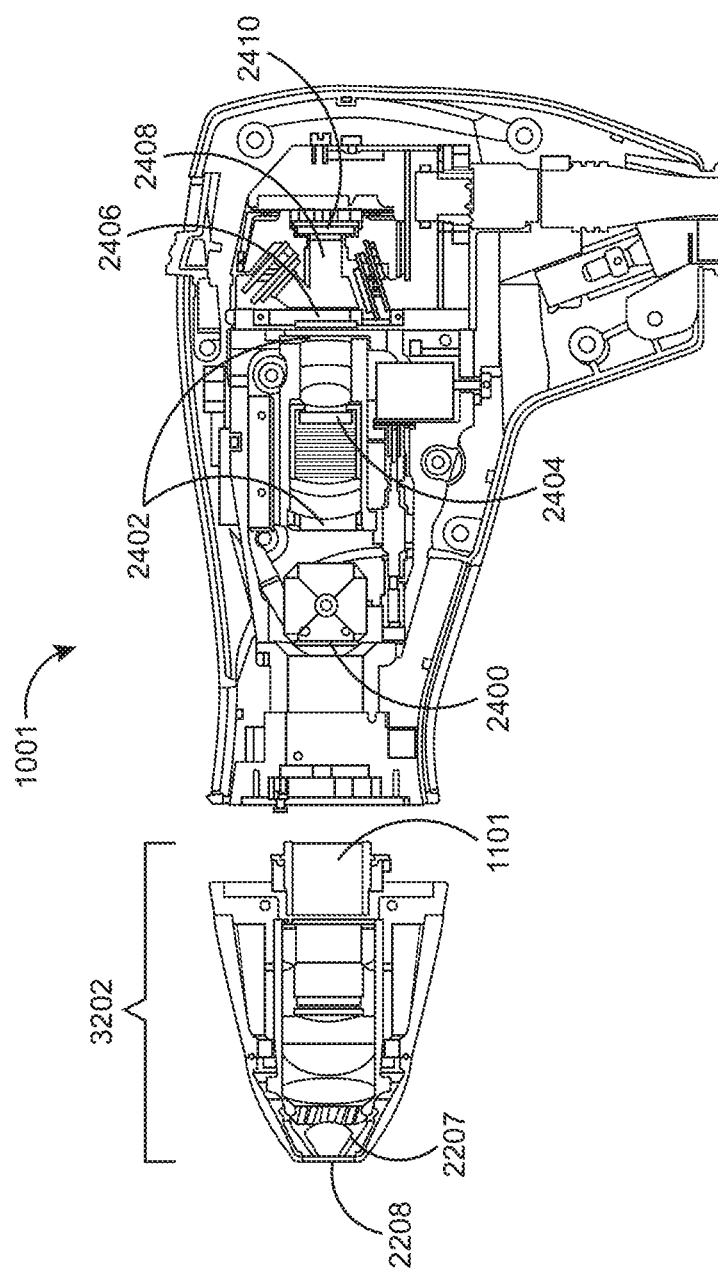
FIG. 7B depicts a lenspiece just separated from a handpiece, including a detailed view of the contact lens, cone shaped lens, intermediate image plane, FA filter/optic window, focus group, aperture stop, IR block filter, color splitting prism spacer block, and image sensors according to one embodiment of the present invention.
Figure 7C:
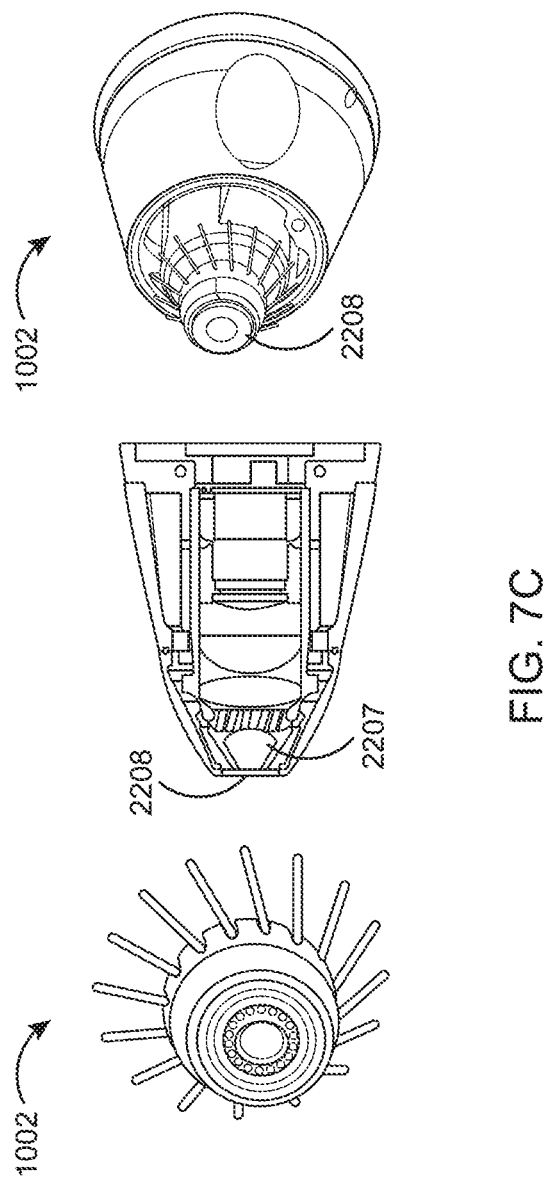
FIG. 7C depicts a lenspiece interior and lenspiece exterior, depicting the skewed fiber array next to the contact lens inside the lenspiece according to one embodiment of the present invention.

In some embodiments, as shown in FIGS. 7A-C, the lenspiece 3202 and handpiece 1001 include detailed exterior and interior core elements essential to the functioning of the eye imaging apparatus. For example, as shown in FIG. 7B, the lenspiece 3202 and handpiece 1001 include a contact lens 2208, cone shaped lens 2207, intermediate image plane 1101, FA filter/optic window 2400, focus group 2402, aperture stop 2404, IR block filter 2406, color splitting prism spacer block 2408, and image sensors 2410.

As described herein, the present invention contemplates optical fibers with high numerical aperture (NA), skewed pointing angles, and light spatial intensity distribution conversion. As a result, the illumination light can span a wide enough range with desired intensity distribution to cover the desired angular field of view on a retina. As described above, in order to convert a bell-shaped distribution to a more top-hat or square-shaped distribution, a thin prism array film based light intensity distribution convertor is used in coupling the illumination light between the handpiece and the lenspiece. By pointing the circular fiber array ends such that light output pointing lines thereof are at a skew angle relative to the lenspiece imaging optical axis, illumination light specularly reflected back from the optical interfaces of the cornea and the ocular lens can be directed away from the imaging path to substantially reduce optical background noise on the image sensor.

The foregoing description of the present invention has been presented for the purpose of illustration and description. It is not intended to be exhaustive or to limit the invention to the precise form disclosed. Many modifications and variations are possible in light of the above teachings. It is intended that the scope of the present invention not be limited by this detailed description, but by the claims and the equivalents to the claims appended hereto.

What is claimed is:

1. A prism array light redistribution apparatus for an eye imaging system comprising:
light transmitting fibers;
light receiving fibers; and
a micro prism array optically coupled to bridge the light transmitting fibers and the light receiving fibers, configured to receive light having a bell-shaped angular distribution from the light transmitting fibers and refract the received light to enter the light receiving fibers such that a square-shaped angular distribution of light emits from a light emitting end of the light receiving fibers.

2. The apparatus of claim 1 further comprising a homogenizer optically coupled to the light transmitting fibers configured to increase uniformity in spatial light intensity distribution of light passing therethrough.

3. The apparatus of claim 2 wherein the homogenizer is a glass rod homogenizer.

4. The apparatus of claim 1 further comprising an optical window optically coupled to the micro prism array.

5. The apparatus of claim 4 wherein the micro prism array comprises a film comprising a prism array.

6. The apparatus of claim 5 wherein the film has a refractive index of 1.66.

7. The apparatus of claim 5 further comprising a glue configured to adhere the film to at least one of the optical window and the light receiving fibers.

8. The apparatus of claim 7 wherein the glue has a refractive index of 1.348.

9. An eye illuminating apparatus comprising:
a handpiece comprising:
a light source;
a plurality of light transmitting fibers optically coupled to the light source;
a focusing lens; and
an image sensor optically aligned with the focusing lens;
a lenspiece comprising:
a plurality of light receiving fibers;
a micro prism array optically coupled to bridge the light transmitting fibers and the light receiving fibers, configured to receive light having a bell-shaped angular distribution from the light transmitting fibers and refract the received light to enter the light receiving fibers such that a square-shaped angular distribution of light emits from a light emitting end of the light receiving fibers; and
an imaging lens optically aligned with the focusing lens;
wherein the focusing lens and the imaging lens combine to define an imaging path of the eye illuminating apparatus; and
wherein the imaging path is positioned such that light emitted by the plurality of light receiving fibers is at least one of reflected and scattered by an eye structure of a patient, refracted through the imaging path, and is incident upon the image sensor.

10. The apparatus of claim 9 wherein the handpiece further comprises a homogenizer optically coupled to the light transmitting fibers configured to increase uniformity in spatial light intensity distribution of light passing therethrough.

11. The apparatus of claim 10 wherein the homogenizer is a glass rod homogenizer.

12. The apparatus of claim 9 wherein the lenspiece further comprises an optical window optically coupled to the micro prism array.

13. The apparatus of claim 12 wherein the micro prism array comprises a film comprising a prism array.

14. The apparatus of claim 13 wherein the film has a refractive index of 1.66.

15. The apparatus of claim 13 further comprising a glue configured to adhere the film to at least one of the optical window and the light receiving fibers.

16. The apparatus of claim 15 wherein the glue has a refractive index of 1.348.

17. The apparatus of claim 9 wherein:
the imaging lens comprises:
   a contact lens;
   a conic lens;
   a mid-position singlet; and
   a back-position doublet; and
the focusing lens comprises an axially movable lens combination comprising:
   a front-position doublet; and
   a back-position triplet.

18. A prism array light redistribution apparatus for an eye imaging system comprising:
light transmitting fibers;
light receiving fibers;
a glass-rod homogenizer optically coupled to the light transmitting fibers configured to increase uniformity in spatial light intensity distribution of light passing therethrough to enter the light receiving fibers; and
a micro prism array optically coupled to bridge the light transmitting fibers and the light receiving fibers, comprising:
   a film comprising a prism array;
   wherein the film is configured to receive light having a bell-shaped angular distribution from the light transmitting fibers and refract the received light to enter the light receiving fibers such that a square-shaped angular distribution of light emits from a light emitting end of the light receiving fibers;
an optical window optically coupled to the micro prism array; and
glue configured to adhere the film to at least one of the optical window and the light receiving fibers.

19. The apparatus of claim 18 wherein the film has a refractive index of 1.66.

20. The apparatus of claim 18 wherein the glue has a refractive index of 1.348.

* * * * *